US008021437B2

(12) United States Patent
Miracle et al.

(10) Patent No.: US 8,021,437 B2
(45) Date of Patent: *Sep. 20, 2011

(54) ORGANIC CATALYST WITH ENHANCED ENZYME COMPATIBLITY

(75) Inventors: Gregory Scot Miracle, Hamilton, OH (US); George Douglas Hiler, II, Harrison, OH (US); Rebecca Massie Grey, West Alexandria, OH (US); Mark Robert Sivik, Mason, OH (US); Ludwig Voelkel, Limbergerhof (DE); Frank Dietsche, Schriesheim (DE); Christian Bittner, Mannheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/468,907

(22) Filed: May 20, 2009

(65) Prior Publication Data

US 2009/0222999 A1    Sep. 10, 2009

Related U.S. Application Data

(63) Continuation of application No. 11/272,276, filed on Nov. 10, 2005, now Pat. No. 7,557,076, which is a continuation-in-part of application No. 10/447,506, filed on May 29, 2003, now Pat. No. 7,169,744.

(60) Provisional application No. 60/691,621, filed on Jun. 17, 2005, provisional application No. 60/386,692, filed on Jun. 6, 2002, provisional application No. 60/426,549, filed on Nov. 15, 2002.

(51) Int. Cl.
*D06L 1/00* (2006.01)
*C11D 3/39* (2006.01)

(52) U.S. Cl. .......................................... 8/137; 510/309

(58) Field of Classification Search ........................ None
See application file for complete search history.

(56) References Cited

U.S. PATENT DOCUMENTS

| | | |
|---|---|---|
| 3,822,114 A | 7/1974 | Montgomery et al. |
| 4,001,131 A | 1/1977 | Montgomery et al. |
| 4,096,141 A | 6/1978 | Milkowski et al. |
| 4,194,987 A | 3/1980 | Brubaker |
| 4,325,957 A | 4/1982 | Zeugner et al. |
| 4,430,243 A | 2/1984 | Bragg et al. |
| 4,505,908 A | 3/1985 | Zeugner et al. |
| 4,595,531 A | 6/1986 | Milkowski et al. |
| 4,977,252 A | 12/1990 | Chiu |
| 5,041,232 A | 8/1991 | Batal et al. |
| 5,045,223 A | 9/1991 | Batal et al. |
| 5,047,163 A | 9/1991 | Batal et al. |
| 5,310,925 A | 5/1994 | Batal et al. |
| 5,354,559 A | 10/1994 | Morehouse |
| 5,360,568 A | 11/1994 | Madison et al. |
| 5,360,569 A | 11/1994 | Madison et al. |
| 5,370,826 A | 12/1994 | Madison et al. |
| 5,413,733 A | 5/1995 | Nicholson et al. |
| 5,442,066 A | 8/1995 | Madison et al. |
| 5,478,357 A | 12/1995 | Madison et al. |
| 5,482,515 A | 1/1996 | Madison et al. |
| 5,486,303 A | 1/1996 | Capeci et al. |
| 5,489,392 A | 2/1996 | Capeci et al. |
| 5,516,448 A | 5/1996 | Capeci et al. |
| 5,550,256 A | 8/1996 | Madison et al. |
| 5,565,422 A | 10/1996 | Del Grecco et al. |
| 5,569,645 A | 10/1996 | Dinniwell et al. |
| 5,574,005 A | 11/1996 | Welch et al. |
| 5,576,282 A | 11/1996 | Miracle et al. |
| 5,576,448 A | 11/1996 | Van Daele et al. |
| 5,595,967 A | 1/1997 | Miracle et al. |
| 5,597,936 A | 1/1997 | Perkins et al. |
| 5,620,969 A | 4/1997 | Bronson et al. |
| 5,652,207 A | 7/1997 | Ghatlia |
| 5,691,297 A | 11/1997 | Nassano et al. |
| 5,692,650 A | 12/1997 | Wolter et al. |
| 5,693,603 A | 12/1997 | Ghatlia |
| 5,710,116 A | 1/1998 | Miracle et al. |
| 5,753,599 A | 5/1998 | Coope et al. |
| 5,760,222 A | 6/1998 | Coope |
| 5,817,614 A | 10/1998 | Miracle et al. |
| 5,835,826 A | 11/1998 | Okada et al. |
| 5,879,584 A | 3/1999 | Bianchetti et al. |
| 5,935,826 A | 8/1999 | Bluc et al. |
| 5,952,282 A | 9/1999 | Löffler et al. |
| 6,007,583 A | 12/1999 | Nestler |
| 6,093,712 A | 7/2000 | Matiskella et al. |
| 6,103,685 A | 8/2000 | Hall |

(Continued)

FOREIGN PATENT DOCUMENTS

CA   1122980   5/1982

(Continued)

OTHER PUBLICATIONS

Coe, E.M., et al., An Investigation of the Chlorination of Some Alcohols Using High Oxidation State Early d-Block Metal Chlorides, Polyhedron, 1992, 11(24) pp. 3123-3128.
W. Whaley et al., The Preparation of 3,4 Dihydroisoquinolines and Related Compounds by the Bischler-Napieralski Reaction, Organic reactions (1951), VI 74-150.
Lee et al., Tetrahedron Letters, 1996, vol. 37, No. 21, pp. 3663-3666.
Allevi et al., A Simple and Convenient Transformation of L-lysine into Pyridinoline and Deoxpyridinoline, two collagen cross-links of Biochemical Interest, Tetrahedron: Asymmetry 13, (2002) 1091-1910.
La Berre, Andre, "Alpha- Sulfocarboylic acids and derivatives. III. Sulfonation and Chlorosulfonation of Acrylic and 3-Chloropropionic Acids" Bulletin de la Societe Chimique de France (1973), (7-8) (Pt. 2), 2266-2269.

(Continued)

*Primary Examiner* — Kamal Saeed
(74) *Attorney, Agent, or Firm* — Andrew J. Mueller; James F. McBride; Leonard W. Lewis

(57) ABSTRACT

This invention relates to cleaning compositions comprising organic catalysts having enhanced enzyme compatibility and processes for making and using such cleaning compositions.

2 Claims, No Drawings

U.S. PATENT DOCUMENTS

| | | | |
|---|---|---|---|
| 6,120,557 A | 9/2000 | Nestler | |
| 6,225,464 B1 | 5/2001 | Hiler, II et al. | |
| 6,306,812 B1 | 10/2001 | Perkins et al. | |
| 6,326,348 B1 | 12/2001 | Vinson et al. | |
| 6,413,920 B1 | 7/2002 | Bettiol et al. | |
| 6,818,607 B1 | 11/2004 | Dykstra et al. | |
| 6,821,935 B1 | 11/2004 | Dykstra et al. | |
| 6,825,160 B1 | 11/2004 | Dykstra et al. | |
| 6,887,838 B2 | 5/2005 | Dykstra et al. | |
| 6,903,060 B1 | 6/2005 | Dykstra et al. | |
| 7,109,156 B1 | 9/2006 | Dykstra et al. | |
| 7,169,744 B2 | 1/2007 | Miracle et al. | |
| 7,501,389 B2 | 3/2009 | Hage et al. | |
| 7,504,371 B2 * | 3/2009 | Miracle et al. | 510/320 |
| 7,507,700 B2 | 3/2009 | Miracle et al. | |
| 7,557,076 B2 | 7/2009 | Miracle et al. | |
| 2002/0123445 A1 | 9/2002 | Dykstra et al. | |
| 2005/0009719 A1 | 1/2005 | Dykstra et al. | |
| 2005/0070454 A1 | 3/2005 | Dykstra et al. | |
| 2005/0113246 A1 | 5/2005 | Hiler II, et al. | |
| 2005/0181969 A1 | 8/2005 | Mort, III et al. | |
| 2005/0256017 A1 | 11/2005 | Dykstra | |
| 2006/0089284 A1 | 4/2006 | Miracle et al. | |
| 2006/0211590 A1 | 9/2006 | Miracle et al. | |
| 2006/0252667 A1 | 11/2006 | Mort, III et al. | |
| 2007/0197417 A1 | 8/2007 | Miracle | |
| 2007/0197421 A1 | 8/2007 | Miracle | |
| 2008/0200682 A1 | 8/2008 | Schein et al. | |
| 2008/0214819 A1 | 9/2008 | Volkel et al. | |
| 2009/0143272 A1 | 6/2009 | Miracle et al. | |
| 2009/0149366 A1 | 6/2009 | Miracle et al. | |

FOREIGN PATENT DOCUMENTS

| | | |
|---|---|---|
| JP | 06-308655 | 11/1994 |
| WO | WO 95/13351 A1 | 5/1995 |
| WO | WO 95/13352 A1 | 5/1995 |
| WO | WO 95/13353 A1 | 5/1995 |
| WO | WO 95/28399 A1 | 10/1995 |
| WO | WO 97/06147 A1 | 2/1997 |
| WO | WO 97/10323 A1 | 3/1997 |
| WO | WO 97/11151 A1 | 3/1997 |
| WO | WO 98/07825 A2 | 2/1998 |
| WO | WO 98/15535 A1 | 4/1998 |
| WO | WO 98/16614 A1 | 4/1998 |
| WO | WO 98/23602 A1 | 6/1998 |
| WO | WO 98/23717 A2 | 6/1998 |
| WO | WO 00/32601 A2 | 6/2000 |
| WO | WO 00/42156 A1 | 7/2000 |
| WO | WO 01/16110 A1 | 3/2001 |
| WO | WO 01/16263 A2 | 3/2001 |
| WO | WO 01/16273 A1 | 3/2001 |
| WO | WO 01/16274 A1 | 3/2001 |
| WO | WO 01/16275 A1 | 3/2001 |
| WO | WO 01/16276 A1 | 3/2001 |
| WO | WO 01/16277 A1 | 3/2001 |
| WO | WO 01/16278 A1 | 3/2001 |
| WO | WO 03/104199 A2 | 12/2003 |
| WO | WO 2007/001261 A1 | 1/2007 |
| WO | WO 2007/001262 A1 | 1/2007 |

OTHER PUBLICATIONS

Mangalagiu et al., 4-Methylpyrimidinium Ylides II, Selective Reactions of Pyrimidinium Ylides with Activated Alkynes, AI, I. Cuza, University, Organic Chemistry Dept, (2000) pp. 2047-2050.

Korshin, E. E., The Reaction of Tertiary Amines With Maleic Acid and Monoalkyl Maleates, Zhurnal Obshchei Khimii, vol. 60(122), No. 5 (May 1990), pp. 1170-1175.

Zugravescu, M, Die Addition Von Philodienen An Phthalazin, Revue Roumaine de Chimi, 12, (1967) pp. 109-116.

Rucinschi, E, Dienophile Addition An Heterozyklischen Verbindungen II, Revue Roumaine deChimie, vol. 13, No. 5, (1968), pp. 637-646.

Undheim, K, Pyridinium-3-Oxide Derivatives From Amino Acids, Part IX, N-Quaternary Compounds, Acta Chemica Scandinavica 23 ( 1969) pp. 2475-2487.

Undheim, K, The Menschutkin Reaction, Part XIX, N-Quaternary Compounds, Acta Chemica Scandinavica, 25, (1971) pp. 18-26.

Le Berre, A, Acides à-SULFO β-Amino Carbozyliques (Taurines à-Carboyzliques), Bull Soc. Chim, FR, (1974) pp. 221-224.

Wittmann, H, Reactions With Betaine, VII; Reactions of Ethyl Malonate-Enolbetaines With Phenyl Isocyanate, Monatschefte fur Chemie 102, (1971), pp. 1120-1128.

Acheson, R.M., Addition Reactions of Heterocyclic Compounds, XVII, The structures and reactions of adducts from pyridines, dimethyl acetylenedicarboxylate, and carbon dioxide at low temperatures, Univ. of Oxford, Journal of the Chemical Society, Abstracts (1964).

H. Böhme et al., *Uber Derivate des 1,2,3,4,5-Pentahydro-2-benzazepins*, Arch Pharm, vol. 306 (4), 1972, pp. 271-274.

* cited by examiner

ORGANIC CATALYST WITH ENHANCED ENZYME COMPATIBLITY

CROSS-REFERENCES TO RELATED APPLICATIONS

This application is a continuation of and claims priority under 35 U.S.C. §120 to U.S. patent application Ser. No. 11/272,276 filed Nov. 10, 2005, which in turn claims priority under 35 U.S.C. §119(e) to U.S. Provisional Application Ser. No. 60/691,621 filed Jun. 17, 2005, and is a continuation-in-part of and claims priority under 35 U.S.C. §120 to U.S. patent application Ser. No. 10/447,506 filed May 29, 2003, which in turn claims priority under 35 U.S.C. §119(e) to U.S. Provisional Application Ser. No. 60/386,692 filed Jun. 6, 2002, and U.S. Provisional Application Ser. No. 60/426,549 filed Nov. 15, 2002.

FIELD OF INVENTION

This invention relates to cleaning compositions comprising organic catalysts and processes for making and using such cleaning products.

BACKGROUND OF THE INVENTION

Oxygen bleaching agents, for example hydrogen peroxide, are typically used to facilitate the removal of stains and soils from clothing and various surfaces. Unfortunately such agents are extremely temperature rate dependent. As a result, when such agents are employed in colder solutions, the bleaching action of such solutions is markedly decreased.

In an effort to resolve the aforementioned performance problem, the industry developed a class of materials known as "bleach activators". However, as such materials rapidly lose their effectiveness at solution temperatures of less than 40° C., new organic catalysts such as 3,4-dihydro-2-[2-(sulfooxy) decyl]isoquinolinium, inner salt were developed. In general, while such current art catalysts are effective in lower temperature water conditions, they can inactivate certain enzymes. As most laundry and cleaning compositions are formulated with enzymes, formulating cleaning products with such catalysts can be problematic.

Accordingly, there is a need for an inexpensive cleaning composition comprising an organic catalyst that can provide the combined benefits of formulation flexibility, low water temperature bleaching performance and enzyme compatibility.

SUMMARY OF THE INVENTION

The present invention relates to cleaning compositions comprising organic catalysts having enhanced enzyme compatibility, and methods of making and using same.

DETAILED DESCRIPTION OF THE INVENTION

Definitions

As used herein, the term "cleaning composition" includes, unless otherwise indicated, granular or powder-form all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, laundry bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the phrase "is independently selected from the group consisting of . . . " means that moieties or elements that are selected from the referenced Markush group can be the same, can be different or any mixture of elements.

The test methods disclosed in the Test Methods Section of the present application must be used to determine the respective values of the parameters of Applicants' inventions.

Unless otherwise noted, all component or composition levels are in reference to the active level of that component or composition, and are exclusive of impurities, for example, residual solvents or by-products, which may be present in commercially available sources.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited are, in relevant part, incorporated herein by reference; the citation of any document is not to be construed as an admission that it is prior art with respect to the present invention.

Cleaning Compositions Comprising Organic Catalyst

Applicants have found that judicious selection of the $R^1$ moiety of the organic catalyst of the present invention results in improved enzyme compatibility. While not being bound by theory, Applicants believe this is due to favorable partitioning of the catalyst in aqueous environments as a result of the aforementioned judicious selection of the $R^1$ moiety.

In one aspect of Applicants' invention, Applicants' cleaning compositions comprise an organic catalyst having an enzyme compatibility value of 70 or greater, or even 80 or greater.

In one aspect of Applicants' invention, Applicants' cleaning compositions comprise an organic catalyst having Formula 1 or Formula 2 below or mixtures thereof.

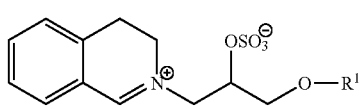

Formula 1

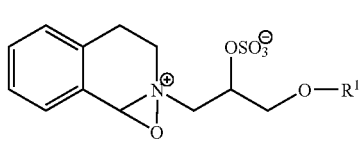

Formula 2 wherein $R_1$ is a branched alkyl group containing from 9 to 24 carbons or linear alkyl group containing from 11 to 24 carbons; a branched alkyl group containing from 9 to 18 carbons or linear alkyl group containing from 11 to 18 carbons; is selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl; or is selected from the group consisting of 2-butyloctyl, 2-pentylnonyl, 2-hexyldecyl, iso-tridecyl and iso-pentadecyl.

The balance of any aspects of the aforementioned cleaning compositions is made up of one or more adjunct materials.

Processes of Making Suitable Organic Catalysts

Suitable organic catalysts can be produced using a variety of reaction vessels and processes including batch, semi-batch and continuous processes.

In one aspect of Applicants invention, the process of making the aforementioned catalyst comprises the step of reacting 3,4-dihydroisoquinoline sulfur trioxide complex with an epoxide to form said organic catalyst.

In another aspect of Applicants' invention, the process of making the aforementioned catalyst comprises the steps of reacting 3,4-dihydroisoquinoline with a material selected from the group consisting of sulfur trioxide, a material that provides sulfur trioxide and mixtures thereof, to form a 3,4-dihydroisoquinoline sulfur trioxide complex, and reacting such 3,4-dihydroisoquinoline sulfur trioxide complex with an epoxide to form said organic catalyst.

In another aspect of Applicants' invention, the process of making the aforementioned catalyst comprises the step of reacting 3,4-dihydroisoquinoline with an epoxide sulfur trioxide complex to form said organic catalyst.

In another aspect of Applicants' invention, the process of making the aforementioned catalyst comprises the steps of reacting an epoxide with a material selected from the group consisting of sulfur trioxide, a material that provides sulfur trioxide and mixtures thereof, to form an epoxide sulfur trioxide complex, and reacting such epoxide sulfur trioxide complex with 3,4-dihydroisoquinoline to form said organic catalyst.

The oxaziridinium ring containing version of the aforementioned catalyst may be produced by contacting an iminium ring containing version of said catalyst with an oxygen transfer agent such as a peroxycarboxylic acid or a peroxymonosulfuric acid, for example, Oxone®. Such species can be formed in situ and used without purification.

While the skilled artisan who processes the teachings of this specification can easily determine the desired reaction conditions and reactant concentrations, typical reaction parameters for the aforementioned aspects of Applicants' invention include reaction temperatures of from about 0° C. to about 150° C., or from about 0° C. to about 125° C., reaction pressures of from about 0.1 to about 100 atmospheres, from about 0.3 atmospheres to about 10 atmospheres or from about 1 atmosphere to about 10 atmospheres; reaction times of 0.1 hours to about 96 hours, from about 1 hour to about 72 hours, or from about 1 hour to about 24 hours. The reaction may also be run under an inert atmosphere or otherwise anhydrous conditions including, when a solvent is employed, the use of an anhydrous solvent.

Materials that are employed in practicing Applicants' process include 3,4-dihydroisoquinoline; epoxides and mixtures thereof; sulfur trioxide, sources of sulfur trioxide and mixtures thereof; and solvents.

When 3,4-dihydroisoquinoline is employed, the initial reaction mixture typically comprises from about 0.5 weight % to about 70 weight %, from about 5 weight % to about 70 weight %, or from about 10 weight % to about 50 weight % of such material. 3,4-Dihydroisoquinoline can be made according to the protocol found in Example 1.

When epoxides are employed, the initial reaction mixture typically comprises from about 0.5 weight % to about 70 weight %, from about 5 weight % to about 70 weight %, or from about 10 weight % to about 50 weight % of such material. Suitable epoxides include but are not limited to epoxides such as 2-propylheptyl glycidyl ether; 2-butyloctyl glycidyl ether; 2-pentylnonyl glycidyl ether; 2-hexyldecyl glycidyl ether; n-dodecyl glycidyl ether; n-tetradecyl glycidyl ether; n-hexadecyl glycidyl ether; n-octadecyl glycidyl ether; iso-nonyl glycidyl ether; iso-decyl glycidyl ether; iso-tridecyl glycidyl ether, and mixtures thereof. Such materials may contain oligomeric forms of the glycidyl ether which may optionally be removed prior to being employed as a reactant. 2-Propylheptyl glycidyl ether can be prepared as described in Example 2 of this specification. All of the other aforementioned glycidyl ethers can be prepared by following the generic protocol of Example 2 by substituting the appropriate alcohol in place of 2-propylheptanol. Suitable alcohols include 2-propylheptanol, 2-butyloctanol, 2-pentylnonanol, 2-hexyldecanol, n-dodecanol, n-tetradecanol, n-hexadecanol, n-octadecanol, iso-nonanol, iso-decanol and iso-tridecanol.

When sulfur trioxide, sources of sulfur trioxide and mixtures thereof are employed, the initial reaction mixture typically comprises from about 0.5 weight % to about 70 weight %, from about 5 weight % to about 70 weight %, or from about 10 weight % to about 50 weight % of such material. Suitable materials include sulfur trioxide, and sulfur trioxide complexes such as sulfur trioxide trimethylamine, sulfur trioxide dioxane, sulfur trioxide pyridine, sulfur trioxide N,N-dimethylformamide, sulfur trioxide sulfolane, sulfur trioxide tetrahydrofuran, sulfur trioxide diethylether, sulfur trioxide 3,4-dihydroisoquinoline and mixtures thereof.

The balance of any reaction mixture is typically solvent. When a solvent is employed, the initial reaction mixture typically comprises up to 99 weight % solvent, from about 10 weight % to about 90 weight % solvent, or from about 20 weight % to about 80 weight % solvent. Suitable solvents include aprotic, polar and apolar solvents such as acetonitrile, dioxane, tertbutyl methylether, tetrahydrofuran, N,N-dimethylformamide, sulfolane, chlorobenzene, toluene, 1,2-dichloroethane, methylene chloride, chloroform, diethyl ether, hexanes, pentanes, benzene, xylenes and mixtures thereof. Suitable solvents can be purchased from Aldrich, P.O. Box 2060, Milwaukee, Wis. 53201, USA.

Cleaning Compositions and Cleaning Composition Additives Comprising Applicants' Organic Catalysts The cleaning composition of the present invention may be advantageously employed for example, in laundry applications, hard surface cleaning, automatic dishwashing applications, as well as cosmetic applications such as dentures, teeth, hair and skin. However, due to the unique advantages of both increased effectiveness in lower temperature solutions and the superior enzyme compatibility, the organic catalysts of the present invention are ideally suited for laundry applications such as the bleaching of fabrics through the use of bleach containing detergents or laundry bleach additives. Furthermore, the organic catalysts of the present invention may be employed in both granular and liquid compositions.

The organic catalysts of the present invention may also be employed in a cleaning additive product. A cleaning additive product including the organic catalysts of the present invention is ideally suited for inclusion in a wash process when additional bleaching effectiveness is desired. Such instances may include but, are not limited to, low temperature solution cleaning application. The additive product may be, in its simplest form, Applicants' organic catalyst. Preferably, the additive could be packaged in dosage form for addition to a cleaning process where a source of peroxygen is employed and increased bleaching effectiveness is desired. Such single dosage form may comprise a pill, tablet, gelcap or other single dosage unit such as pre-measured powders or liquids. A filler or carrier material may be included to increase the volume of such composition. Suitable filler or carrier materials include, but are not limited to, various salts of sulfate, carbonate and silicate as well as talc, clay and the like. Filler or carrier materials for liquid compositions may be water or low molecular weight primary and secondary alcohols including polyols and diols. Examples of such alcohols include, but are not limited to, methanol, ethanol, propanol and isopropanol. The compositions may contain from about 5% to about 90% of such materials. Acidic fillers can be used to reduce pH. Alternatively, the cleaning additive may include an activated peroxygen source defined below or the adjunct ingredients as fully defined below.

Applicants' cleaning compositions and cleaning additives require a catalytically effective amount of Applicants' organic catalyst. The required level of such catalyst may be achieved by the addition of one or more species of Applicants' organic catalyst. As a practical matter, and not by way of limitation, the compositions and cleaning processes herein can be adjusted to provide on the order of at least 0.001 ppm, from about 0.001 ppm to about 500 ppm, from about 0.005 ppm to about 150 ppm, or even from about 0.05 ppm to about 50 ppm of Applicants' organic catalyst in the wash liquor. In order to obtain such levels in the wash liquor, typical compositions herein may comprise from about 0.0002% to about 5%, or even from about 0.001% to about 1.5%, of organic catalyst, by weight of the cleaning compositions.

When the Applicants' organic catalyst is employed in a granular composition, it may be desirable for the Applicants' organic catalyst to be in the form of an encapsulated particle to protect the Applicants' organic catalyst from moisture and/or other components of the granular composition during storage. In addition, encapsulation is also a means of controlling the availability of the Applicants' organic catalyst during the cleaning process and may enhance the bleaching performance of the Applicants' organic catalyst. In this regard, the Applicants' organic catalyst can be encapsulated with any encapsulating material known in the art.

The encapsulating material typically encapsulates at least part, preferably all, of the Applicants' organic catalyst. Typically, the encapsulating material is water-soluble and/or water-dispersible. The encapsulating material may have a glass transition temperature (Tg) of 0° C. or higher.

The encapsulating material is preferably selected from the group consisting of carbohydrates, natural or synthetic gums, chitin and chitosan, cellulose and cellulose derivatives, silicates, phosphates, borates, polyvinyl alcohol, polyethylene glycol, paraffin waxes and combinations thereof. Preferably the encapsulating material is a carbohydrate, typically selected from the group consisting of monosaccharides, oligosaccharides, polysaccharides, and combinations thereof. Most preferably, the encapsulating material is a starch. Preferred starches are described in EP 0 922 499; U.S. Pat. No. 4,977,252; U.S. Pat. No. 5,354,559 and U.S. Pat. No. 5,935,826.

The encapsulating material may be a microsphere made from plastic such as thermoplastics, acrylonitrile, methacrylonitrile, polyacrylonitrile, polymethacrylonitrile and mixtures thereof; commercially available microspheres that can be used are those supplied by Expancel of Stockviksverken, Sweden under the trademark Expancel®, and those supplied by PQ Corp. of Valley Forge, Pa. USA under the tradename PM 6545, PM 6550, PM 7220, PM 7228, Extendospheres®, Luxsil®, Q-cel® and Sphericel®.

The cleaning compositions herein will preferably be formulated such that, during use in aqueous cleaning operations, the wash water will have a pH of between about 6.5 and about 11, or even about 7.5 and 10.5. Liquid dishwashing product formulations may have a pH between about 6.8 and about 9.0. Laundry products typically have a pH of from about 9 to about 11. Techniques for controlling pH at recommended usage levels include the use of buffers, alkalis, acids, etc., and are well known to those skilled in the art.

Adjunct Materials

While not essential for the purposes of the present invention, the non-limiting list of adjuncts illustrated hereinafter are suitable for use in the instant compositions and may be desirably incorporated in certain embodiments of the invention, for example to assist or enhance cleaning performance, for treatment of the substrate to be cleaned, or to modify the aesthetics of the cleaning composition as is the case with perfumes, colorants, dyes or the like. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, solvents and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential to Applicants' compositions. Thus, certain embodiments of Applicants' compositions do not contain one or more of the following adjuncts materials: surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, solvents and/or pigments. However, when one or more adjuncts are present, such one or more adjuncts may be present as detailed below:

Bleaching Agents—The cleaning compositions of the present invention may comprise one or more bleaching agents. Suitable bleaching agents other than bleaching catalysts include photobleaches, bleach activators, hydrogen peroxide, sources of hydrogen peroxide, pre-formed peracids and mixtures thereof. In general, when a bleaching agent is used, the compositions of the present invention may comprise from about 0.1% to about 50% or even from about 0.1% to about 25% bleaching agent by weight of the subject cleaning composition. Examples of suitable bleaching agents include:

(1) photobleaches for example sulfonated zinc phthalocyanine;

(2) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxzone®, and mixtures thereof. Suitable percarboxylic acids include hydrophobic and hydrophilic peracids having the formula R—(C=O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen;

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall composition and are typically incorporated into such compositions as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps; and (4) bleach activators having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject cleaning composition may comprise NOBS, TAED or mixtures thereof.

When present, the peracid and/or bleach activator is generally present in the composition in an amount of from about 0.1 to about 60 wt %, from about 0.5 to about 40 wt % or even from about 0.6 to about 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Surfactants—The cleaning compositions according to the present invention may comprise a surfactant or surfactant system wherein the surfactant can be selected from nonionic surfactants, anionic surfactants, cationic surfactants, ampholytic surfactants, zwitterionic surfactants, semi-polar nonionic surfactants and mixtures thereof. When present, surfactant is typically present at a level of from about 0.1% to about 60%, from about 1% to about 50% or even from about 5% to about 40% by weight of the subject composition.

Builders—The cleaning compositions of the present invention may comprise one or more detergent builders or builder systems. When a builder is used, the subject composition will typically comprise at least about 1%, from about 5% to about 60% or even from about 10% to about 40% builder by weight of the subject composition.

Builders include, but are not limited to, the alkali metal, ammonium and alkanolammonium salts of polyphosphates, alkali metal silicates, alkaline earth and alkali metal carbonates, aluminosilicate builders and polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3, 5-tricarboxylic acid, carboxymethyloxysuccinic acid, and soluble salts thereof.

Chelating Agents—The cleaning compositions herein may contain a chelating agent. Suitable chelating agents include copper, iron and/or manganese chelating agents and mixtures thereof. When a chelating agent is used, the subject composition may comprise from about 0.005% to about 15% or even from about 3.0% to about 10% chelating agent by weight of the subject composition.

Dye Transfer Inhibiting Agents—The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Brighteners—The cleaning compositions of the present invention can also contain additional components that may tint articles being cleaned, such as fluorescent brighteners. Suitable fluorescent brightener levels include lower levels of from about 0.01, from about 0.05, from about 0.1 or even from about 0.2 wt % to upper levels of 0.5 or even 0.75 wt %.

Dispersants—The compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

Enzymes—The cleaning compositions can comprise one or more enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is an enzyme cocktail that may comprise, for example, a protease and lipase in conjunction with amylase. When present in a cleaning composition, the aforementioned enzymes may be present at levels from about 0.00001% to about 2%, from about 0.0001% to about 1% or even from about 0.001% to about 0.5% enzyme protein by weight of the composition.

Enzyme Stabilizers—Enzymes for use in detergents can be stabilized by various techniques. The enzymes employed herein can be stabilized by the presence of water-soluble sources of calcium and/or magnesium ions in the finished compositions that provide such ions to the enzymes. In case of aqueous compositions comprising protease, a reversible protease inhibitor, such as a boron compound, can be added to further improve stability.

Catalytic Metal Complexes—Applicants' cleaning compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. No. 5,597,936; U.S. Pat. No. 5,595,967. Such cobalt catalysts are readily prepared by known procedures, such as taught for example in U.S. Pat. No. 5,597,936, and U.S. Pat. No. 5,595,967.

Compositions herein may also suitably include a transition metal complex of ligands such as bispidones (WO 05/042532 A1) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include, for example, manganese, iron and chromium. Suitable MRLs include 5,12-diethyl-1,5,8,12-tetraazabicyclo[6.6.2]hexadecane.

Suitable transition metal MRLs are readily prepared by known procedures, such as taught for example in WO 00/32601, and U.S. Pat. No. 6,225,464.

Solvents—Suitable solvents include water and other solvents such as lipophilic fluids. Examples of suitable lipophilic fluids include siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures thereof.

Processes of Making Cleaning and/or Treatment Compositions

The cleaning compositions of the present invention can be formulated into any suitable form and prepared by any process chosen by the formulator, non-limiting examples of which are described in Applicants' examples and in U.S. Pat. No. 5,879,584; U.S. Pat. No. 5,691,297; U.S. Pat. No. 5,574,005; U.S. Pat. No. 5,569,645; U.S. Pat. No. 5,565,422; U.S. Pat. No. 5,516,448; U.S. Pat. No. 5,489,392; U.S. Pat. No. 5,486,303 all of which are incorporated herein by reference.

Method of Use

The present invention includes a method for cleaning a situs inter alia a surface or fabric. Such method includes the steps of contacting an embodiment of Applicants' cleaning composition, in neat form or diluted in a wash liquor, with at least a portion of a surface or fabric then optionally rinsing such surface or fabric. The surface or fabric may be subjected to a washing step prior to the aforementioned rinsing step. For purposes of the present invention, washing includes but is not limited to, scrubbing, and mechanical agitation. As will be appreciated by one skilled in the art, the cleaning compositions of the present invention are ideally suited for use in laundry applications. Accordingly, the present invention includes a method for laundering a fabric. The method comprises the steps of contacting a fabric to be laundered with a said cleaning laundry solution comprising at least one embodiment of Applicants' cleaning composition, cleaning additive or mixture thereof. The fabric may comprise most any fabric capable of being laundered in normal consumer use conditions. The solution preferably has a pH of from about 8 to about 10.5. The compositions may be employed at concentrations of from about 500 ppm to about 15,000 ppm in solution. The water temperatures typically range from about 5° C. to about 90° C. The water to fabric ratio is typically from about 1:1 to about 30:1.

Organic Catalyst/Enzyme Compatibility Test

The test described below uses an alpha amylase activity assay to measure the impact of organic catalysts on the enzyme.

Equipment. UV/Vis spectrophotometer capable of measuring @ 415 nm, heated magnetic stirrer capable of 40° C., 5 mL Luer lock syringe and filters (Acrodisc 0.45 µm), pH meter, and balance (4-place analytical).

Reagents. Merck Amylase Kit (Merck Eurolab, Cat. No. 1.19718.0001); Trizma Base (Sigma Cat # T-1503, or equivalent); Calcium Chloride Dihydrate (Sigma Cat # C-5080, or equivalent); Sodium Thiosulfate Pentahydrate (Sigma Cat # S-6672 or equivalent); Hydrochloric Acid (VWR Cat # JT9535-0, or equivalent); Hardness solution (CTC Group, 3.00 gr/cc or equivalent); Sodium Percarbonate; Peracetic Acid (Aldrich, Cat. #26933-6 or equivalent); Amylase enzymes: Termamyl, Natalase, and Duramyl (Novozymes, Denmark); Granular detergent matrix containing no enzyme, organic catalyst or bleaching agents.

1.) Solution Preparation: prepare the following:
   a.) TRIS Assay Buffer. Prepare 1 liter of 0.1M TRIS buffer, 0.5% sodium thiosulphate (W/V), 0.11% calcium chloride (w/v) at pH 8.3.
   b.) Blank Detergent Solution. Prepare one liter of 0.5% enzyme and bleach free granular detergent product in deionized water (W/V) that is 250 ppm $H_2O_2$ (0.77 gm percarbonate) and 10 gpg hardness (880 UI of hardness).
   c.) Termamyl, Duramyl and Natalase Stock. Make 100 mL solutions each of a 0.1633 mg active Termamyl per mL TRIS Buffer, a 0.1159 mg active Natalase per mL TRIS Buffer, and a 0.1596 mg active Duramyl per mL TRIS Buffer.
   d.) Organic catalyst stocks. Make a 500 ppm in methanol solution of µm.
   e.) Peracetic acid stock. Make a 3955 ppm peracetic acid solution in deionized water.
   f.) Amylase reagent. Follow Merck kit instructions for preparing flacons (containers) 1 and 2 using flacon 3 and subsequent mixing of flacons 1 and 2 to produce the final reagent used in the amylase activity analysis.
2.) Sample Analysis
   a.) Analysis of sample with enzyme only: Add 100 mL of blank detergent solution to a 150 mL beaker. Place beaker on heated stir plate and bring temperature to 40° C. with stirring. Add Y µL of enzyme stock to the beaker where Y=612 µL for Duramyl, 306 µL for Termamyl, or 918 µL for Natalase. Spike only enzyme of interest. Stir sample for 1 minute. Start timer. At 7 minutes 45 seconds, pull a sample and filter it using a 0.45 μm syringe filter (5 mL syringe). Mix 6 μL of filtered sample with 250 μL of amylase reagent in a cuvette and place the cuvette in a UV/VIS spectrophotometer and monitor change in absorbance at 415 nm. Determine length of time ($t_E$) to the nearest second required to obtain an absorbance reading of 1.0 for each enzyme. Use each enzyme's $t_E$ in Steps 2.)b.) and 2.)c.) below.

b.) Analysis of sample with enzyme and peracetic acid only. Follow Step 2.)a.) except after enzyme addition, allow solution to stir for 1 minute then add 127 μL of peracetic acid stock and start timer. Pull sample at 7 minutes 45 seconds as in Step 2.)a.). Once sample and reagent are mixed, record the absorbance at $t_E$ for the respective enzyme. Designate such absorbance $A_b$.

c.) Analysis of sample with enzyme, peracetic acid, and organic catalyst. Follow Step 2.)a.) except after enzyme addition, allow solution to stir for 1 minute then add 127 μL of peracetic acid stock and 100 μL of organic catalyst stock and start timer. Pull sample at 7 minutes 45 seconds as in Step 2.)a.). Once sample and reagent are mixed, record the absorbance at $t_E$ for the respective enzyme. Designate such absorbance $A_c$.

3.) Calculate Enzyme Compatibility Value (ECV)

a.) Calculate the ECV for each specific enzyme: termamyl ($ECV_{ter}$), duramyl ($ECV_{dur}$) and natalase ($ECV_{nat}$). The ECV for any specific enzyme is $(A_c/A_b) \times 100$ where $A_b$ and $A_c$ are the values determined in Steps 2.)b.) and 2.)c.), respectively, for that enzyme.

b.) The ECV for a given organic catalyst is the average of the individual ECV values for the three enzymes. Thus, $ECV = (ECV_{ter} + ECV_{dur} + ECV_{nat})/3$.

EXAMPLES

Unless otherwise indicated, materials can be obtained from Aldrich, P.O. Box 2060, Milwaukee, Wis. 53201, USA. In Examples 1-12, the solvent acetonitrile may be replaced with other solvents, including but not limited to, 1,2-dichloroethane.

Example 1

Preparation of Sulfuric acid mono-[2-(3,4-dihydro-isoquinolin-2-yl)-1-(2-propylheptyloxymethyl)-ethyl]ester, internal salt Preparation of 2-propylheptyl glycidyl ether: To a flame dried, 500 mL round bottomed flask equipped with an addition funnel charged with epichlorohydrin (15.62 gm., 0.17 moles), is added 2-propylheptanol (Pfaltz & Bauer, Inc., 172 E. Aurora Street, Waterbury Conn., 06708, USA) (20 gm., 0.127 moles) and stannic chloride (0.20 gm., 0.001 moles). The reaction is kept under an argon atmosphere and warmed to 90° C. using an oil bath. Epichlorohydrin is dripped into the stirring solution over 60 minutes followed by stirring at 90° C. for 18 hours. The reaction is fitted with a vacuum distillation head and 1-chloro-3-(2-propyl-heptyloxy)-propan-2-ol is distilled at a temperature range of 90° C.->95° C. under 0.2 mm Hg. Wt.=22.1 gm. The 1-chloro-3-(2-propyl-heptyloxy)-propan-2-ol (5.0 gm., 0.020 moles) is dissolved in tetrahydrofuran (50 mL) and stirred at RT under an argon atmosphere. To the stirring solution is added potassium tert-butoxide (2.52 gm., 0.022 moles) and the suspension is stirred at RT for 18 hours. The reaction is then evaporated to dryness, residue dissolved in hexanes and washed with water (100 mL). The hexanes phase is separated, dried with $Na_2SO_4$, filtered and evaporated to dryness to yield the crude 2-propylheptyl glycidyl ether, which can be further purified by vacuum distillation.

Preparation of Sulfuric acid mono-[2-(3,4-dihydro-isoquinolin-2-yl)-1-(2-propylheptyloxymethyl)-ethyl]ester, internal salt: To a flame dried 250 mL three neck round bottomed flask, equipped with a condenser, dry argon inlet, magnetic stir bar, thermometer, and heating bath is added 3,4-dihydroisoquinoline (0.38 mol prepared as described in Example I of U.S. Pat. No. 5,576,282), 2-propylheptyl glycidyl ether (0.38 mol, prepared as described above), $SO_3$-DMF complex (0.38 mol), and acetonitrile (500 mL). The reaction is warmed to 80° C. and stirred at temperature for 72 hours. The reaction is cooled to room temperature, evaporated to dryness and the residue recrystallized from ethyl acetate and/or ethanol to yield the desired product.

Example 2

Preparation of Sulfuric acid mono-[2-(3,4-dihydro-isoquinolin-2-yl)-1-(2-butyl-octyloxymethyl)-ethyl]ester, internal salt The desired product is prepared according to Example 1, substituting 2-butyloctanol for 2-propylheptanol.

Example 3

Preparation of Sulfuric acid mono-[2-(3,4-dihydro-isoquinolin-2-yl)-1-(2-pentyl-nonyloxymethyl)-ethyl]ester, internal salt The desired product is prepared according to Example 1, substituting 2-pentylnonanol (obtained from Pfaltz & Bauer, Inc., Waterbury, Conn. 06708) for 2-propylheptanol.

Example 4

Preparation of Sulfuric acid mono-[2-(3,4-dihydro-isoquinolin-2-yl)-1-(2-hexyl-decyloxymethyl)-ethyl]ester, internal salt The desired product is prepared according to Example 1, substituting 2-hexyldecanol for 2-propylheptanol.

Example 5

Preparation of Sulfuric acid mono-[2-(3,4-dihydro-isoquinolin-2-yl)-1-(dodecyloxymethyl)-ethyl]ester, internal salt The desired product is prepared according to Example 1, substituting n-dodecanol for 2-propylheptanol.

Example 6

Preparation of Sulfuric acid mono-[2-(3,4-dihydro-isoquinolin-2-yl)-1-(tetradecyloxymethyl)-ethyl]ester, internal salt The desired product is prepared according to Example 1, substituting n-tetradecanol for 2-propylheptanol.

Example 7

Preparation of Sulfuric acid mono-[2-(3,4-dihydro-isoquinolin-2-yl)-1-(hexadecyloxymethyl)-ethyl] ester, internal salt The desired product is prepared according to Example 1, substituting n-hexadecanol for 2-propylheptanol.

Example 8

Preparation of Sulfuric acid mono-[2-(3,4-dihydro-isoquinolin-2-yl)-1-(octadecyloxymethyl)-ethyl] ester, internal salt The desired product is prepared according to Example 1, substituting n-octadecanol for 2-propylheptanol.

Example 9

Preparation of Sulfuric acid mono-[2-(3,4-dihydro-isoquinolin-2-yl)-1-(iso-nonyloxymethyl)-ethyl]ester, internal salt The desired product is prepared according to Example 1, substituting iso-nonanol (Exxal 9 obtained from Exxon Mobile Chemical, Houston, Tex. USA) for 2-propylheptanol.

Example 10

Preparation of Sulfuric acid mono-[2-(3,4-dihydro-isoquinolin-2-yl)-1-(iso-decyloxymethyl)-ethyl]ester, internal salt The desired product is prepared according to Example 1, substituting iso-decanol (obtained from City Chemicals LLC, West Haven, Conn. USA) for 2-propylheptanol.

Example 11

Preparation of Sulfuric acid mono-[2-(3,4-dihydro-isoquinolin-2-yl)-1-(iso-tridecyloxymethyl)-ethyl] ester, internal salt The desired product is prepared according to Example 1, substituting iso-tridecanol (obtained from BASF Corporation, Mount Olive, N.J. USA) for 2-propylheptanol.

Example 12

Simultaneous Preparation of Sulfuric acid mono-[2-(3,4-dihydro-isoquinolin-2-yl)-1-(iso-tridecyloxymethyl)-ethyl]ester, internal salt and Sulfuric acid mono-[2-(3,4-dihydro-isoquinolin-2-yl)-1-(iso-pentadecyloxymethyl)-ethyl]ester, internal salt The desired products are prepared according to Example 1, substituting a mixture of isomeric tridecanols to pentadecanols (obtained from BASF Corporation, Mount Olive, N.J. USA) for 2-propylheptanol.

Example 13

Bleaching detergent compositions having the form of granular laundry detergents are exemplified by the following formulations.

|  | A | B | C | D | E | F |
| --- | --- | --- | --- | --- | --- | --- |
| Linear alkylbenzenesulfonate | 20 | 22 | 20 | 15 | 20 | 20 |
| $C_{12}$ Dimethylhydroxyethyl ammonium chloride | 0.7 | 1 | 1 | 0.6 | 0.0 | 0.7 |
| AE3S | 0.9 | 0.0 | 0.9 | 0.0 | 0.0 | 0.9 |
| AE7 | 0.0 | 0.5 | 0.0 | 1 | 3 | 1 |
| sodium tripolyphosphate | 23 | 30 | 23 | 17 | 12 | 23 |
| Zeolite A | 0.0 | 0.0 | 0.0 | 0.0 | 10 | 0.0 |
| 1.6R Silicate | 7 | 7 | 7 | 7 | 7 | 7 |
| Sodium Carbonate | 15 | 14 | 15 | 18 | 15 | 15 |
| Polyacrylate MW 4500 | 1 | 0.0 | 1 | 1 | 1.5 | 1 |
| Carboxy Methyl Cellulose | 1 | 1 | 1 | 1 | 1 | 1 |
| Savinase 32.89 mg/g | 0.1 | 0.07 | 0.1 | 0.1 | 0.1 | 0.1 |
| Natalase 8.65 mg/g | 0.1 | 0.1 | 0.1 | 0.0 | 0.1 | 0.1 |
| Brightener 15 | 0.06 | 0.0 | 0.06 | 0.18 | 0.06 | 0.06 |
| Brightener 49 | 0.1 | 0.06 | 0.1 | 0.0 | 0.1 | 0.1 |
| Diethylenetriamine pentacetic acid | 0.6 | 0.3 | 0.6 | 0.25 | 0.6 | 0.6 |
| $MgSO_4$ | 1 | 1 | 1 | 0.5 | 1 | 1 |
| Sodium Percarbonate | 0.0 | 5.2 | 0.1 | 0.0 | 0.0 | 0.0 |
| Photobleach | 0.0030 | 0.0015 | 0.0015 | 0.0020 | 0.0045 | 0.0010 |
| Sodium Perborate Monohydrate | 4.4 | 0.0 | 3.85 | 2.09 | 0.78 | 3.63 |
| NOBS | 1.9 | 0.0 | 1.66 | 1.77 | 0.33 | 0.75 |
| TAED | 0.58 | 1.2 | 0.51 | 0.0 | 0.015 | 0.28 |
| Organic Catalyst* | 0.0185 | 0.0185 | 0.0162 | 0.0162 | 0.0111 | 0.0074 |
| Sulfate/Moisture | Balance to 100% | Balance to 100% | Balance to 100% | Balance to 100% | Balance to 100% | Balance to 100% |

*Organic catalyst prepared according to Examples 1 through 12, or mixtures thereof.

Any of the above compositions is used to launder fabrics at a concentration of 3500 ppm in water, 25° C., and a 25:1 water:cloth ratio. The typical pH is about 10 but can be can be adjusted by altering the proportion of acid to Na-salt form of alkylbenzenesulfonate.

Example 14

Bleaching detergent compositions having the form of granular laundry detergents are exemplified by the following formulations.

|  | A | B | C | D |
|---|---|---|---|---|
| Linear alkylbenzenesulfonate | 8 | 7.1 | 7 | 6.5 |
| AE3S | 0 | 4.8 | 0 | 5.2 |
| Alkylsulfate | 1 | 0 | 1 | 0 |
| AE7 | 2.2 | 0 | 3.2 | 0.1 |
| $C_{10-12}$ Dimethyl hydroxyethylammonium chloride | 0.75 | 0.94 | 0.98 | 0.98 |
| Crystalline layered silicate ($\delta$-$Na_2Si_2O_5$) | 4.1 | 0 | 4.8 | 0 |
| Zeolite A | 20 | 0 | 17 | 0 |
| Citric Acid | 3 | 5 | 3 | 4 |
| Sodium Carbonate | 15 | 20 | 14 | 20 |
| Silicate 2R ($SiO_2$:$Na_2O$ at ratio 2:1) | 0.08 | 0 | 0.11 | 0 |
| Soil release agent | 0.75 | 0.72 | 0.71 | 0.72 |
| Acrylic Acid/Maleic Acid Copolymer | 1.1 | 3.7 | 1.0 | 3.7 |
| Carboxymethylcellulose | 0.15 | 1.4 | 0.2 | 1.4 |
| Protease (56.00 mg active/g) | 0.37 | 0.4 | 0.4 | 0.4 |
| Amylase (21.55 mg active/g) | 0.3 | 0.3 | 0.3 | 0.3 |
| Lipase (11.00 mg active/g) | 0 | 0.7 | 0 | 0.7 |
| Tetraacetyl ethylene diamine (TAED) | 3.6 | 4.0 | 3.6 | 4.0 |
| Percarbonate | 13 | 13.2 | 13 | 13.2 |
| Organic Catalyst* | 0.04 | 0.02 | 0.01 | 0.06 |
| Na salt of Ethylenediamine-N,N'-disuccinic acid, (S,S) isomer (EDDS) | 0.2 | 0.2 | 0.2 | 0.2 |
| Hydroxyethane di phosphonate (HEDP) | 0.2 | 0.2 | 0.2 | 0.2 |
| $MgSO_4$ | 0.42 | 0.42 | 0.42 | 0.42 |
| Perfume | 0.5 | 0.6 | 0.5 | 0.6 |
| Suds suppressor agglomerate | 0.05 | 0.1 | 0.05 | 0.1 |
| Soap | 0.45 | 0.45 | 0.45 | 0.45 |
| Sodium sulfate | 22 | 33 | 24 | 30 |
| Sulphonated zinc phtalocyanine | 0.07 | 0.12 | 0.07 | 0.12 |
| Photobleach | 0.0014 | 0.002 | 0.0014 | 0.001 |
| Speckles | 0.03 | 0.05 | 0.03 | 0.05 |
| Water & Miscellaneous | Balance to 100% | Balance to 100% | Balance to 100% | Balance to 100% |

*Organic catalyst prepared according to Examples 1 through 12, or mixtures thereof.

Any of the above compositions is used to launder fabrics at a concentration of 10,000 ppm in water, 20-90° C., and a 5:1 water:cloth ratio. The typical pH is about 10 but can be can be adjusted by altering the proportion of acid to Na-salt form of alkylbenzenesulfonate.

Example 15

Bleaching detergent compositions having the form of granular laundry detergents are exemplified by the following formulations.

|  | A | B | C | D | E | F |
|---|---|---|---|---|---|---|
| Linear Alkylbenzenesulfonate | 19.0 | 15.0 | 20.0 | 19.0 | 18.0 | 17.5 |
| Alkylsulfate | 1.1 | 1.0 | 0.8 | 1.0 | 1.1 | 1.2 |
| AE3S | 0.3 | 0.2 | 0.0 | 0.1 | 0.3 | 0.5 |
| Polyacrylic Acid, partially neutralized | 6.0 | 5.5 | 7.5 | 7.0 | 5.8 | 6.0 |
| Sodium Xylene Sulfonate* | 1.5 | 1.9 | 2.0 | 1.7 | 1.5 | 1.0 |
| PEG 4000 | 0.3 | 0.25 | 0.35 | 0.15 | 0.2 | 0.10 |
| Brightener 49 | 0 | 0 | 0.32 | 0.04 | 0.04 | 0.16 |
| Brightener 15 | 0 | 0 | 0.68 | 0.08 | 0.08 | 0.32 |
| Moisture | 2.50 | 2.00 | 2.90 | 2.20 | 2.40 | 1.80 |
| Sodium carbonate | 20.0 | 17.5 | 21.0 | 20.2 | 19.0 | 18.0 |
| Sodium Sulfate | 0.20 | 0.30 | 0.50 | 0.30 | 0.45 | 0.10 |
| Sodium Silicate | 0.25 | 0.25 | 0.55 | 0.30 | 0.25 | 0.10 |
| Layered Silicate Builder | 2.7 | 3.0 | 2.2 | 3.7 | 1.5 | 1.0 |
| Zeolite A | 11.0 | 11.0 | 12.5 | 10.2 | 9.5 | 8.0 |
| Protease | 0.20 | 0.50 | 1.0 | 0.15 | 0.40 | 0.0 |
| Silicone Suds Suppressor | 0.40 | 0.35 | 1.00 | 0.60 | 0.50 | 0.00 |
| Coarse Sulfate | 21.5 | 23.0 | 21.0 | 21.0 | 20.0 | 18.5 |
| Amine Reaction Product comprising $\delta$-Damascone**** | 0.40 | 0.25 | 0.10 | 0.35 | 0.60 | 0.00 |
| Perfume | 0.10 | 0.30 | 0.20 | 0.20 | 0.40 | 0.50 |
| Sodium Percarbonate | 2.8 | 4.5 | 2.00 | 4.7 | 7.4 | 10.0 |
| Conventional Activator (NOBS) | 2.10 | 3.7 | 1.00 | 3.0 | 5.0 | 10.0 |
| Organic Catalyst** | 0.005 | 0.10 | 1.00 | 0.25 | 0.05 | 0.05 |
| Bluing agent*** | 0.50 | 0.20 | 1.00 | 0.30 | 0.10 | 0.00 |
| Filler | Balance to 100% | Balance to 100% | Balance to 100% | Balance to 100% | Balance to 100% | Balance to 100% |

*Other hydrotropes, such as sodium toluenesulfonate, may also be used.
**Organic catalyst prepared according to Examples 1 through 12, or mixtures thereof.
***Such as Ultramarine Blue or Azo-CM-Cellulose (Megazyme, Bray, Co. Wicklow, Ireland)
****Prepared according to WO 00/02991.

Any of the above compositions is used to launder fabrics at a concentration of 500-1500 ppm in water, 5-25° C., and a 15:1-25:1 water:cloth ratio. The typical pH is about 9.5-10 but can be can be adjusted by altering the proportion of acid to Na-salt form of alkylbenzenesulfonate.

Example 16

The organic catalysts listed below are tested according to Applicants' Organic Catalyst/Enzyme Compatibility Test using [Peracetic Acid]=5.0 ppm; [organic catalyst]=0.5 ppm and the following results are obtained.

| | Catalyst Moiety | Enzyme Compatibility Values | | | |
|---|---|---|---|---|---|
| Entry* | $R^1$ | $ECV_{ter}$ | $ECV_{dur}$ | $ECV_{nat}$ | ECV |
| 1 | tert-butyl | 51 | 86 | 58 | 65 |
| 2 | 2-ethylhexyl | 54 | 90 | 57 | 67 |
| 3 | 2-propylheptyl | 98 | 101 | 99 | 99 |
| 4 | 2-butyloctyl | 101 | 101 | 102 | 101 |
| 5 | $n-C_{12/14}$ | 102 | 100 | 100 | 101 |
| 6 | iso-nonyl | 86 | 96 | 88 | 90 |
| 7 | iso-decyl | 98 | 97 | 96 | 97 |
| 8 | iso-tridecyl | 99 | 100 | 101 | 100 |

*Entries 1 and 2 are respectively $C_4$ and $C_8$ branched alkyl moieties which are not encompassed by Applicants' Formula 1.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cleaning composition comprising an organic catalyst having an enzyme compatibility value of 70 or greater and one or more adjunct ingredients.

2. The cleaning composition of claim 1 comprising an organic catalyst having an enzyme compatibility value of 80 or greater, said composition comprising the following adjunct ingredients: an activated peroxygen source, an enzyme and a surfactant.

* * * * *